United States Patent
Ding et al.

(10) Patent No.: US 8,760,088 B2
(45) Date of Patent: Jun. 24, 2014

(54) ELECTROMAGNETISM-TORQUE FRICTION-BALANCING TRUCKLE FOR MOBILE MEDICAL DEVICES

(75) Inventors: Wei jiang Ding, Beijing (CN); Lihui Jiang, Beijing (CN)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 221 days.

(21) Appl. No.: 13/338,454

(22) Filed: Dec. 28, 2011

(65) Prior Publication Data

US 2012/0161675 A1  Jun. 28, 2012

(30) Foreign Application Priority Data

Dec. 28, 2010 (CN) .......................... 2010 1 0609010

(51) Int. Cl.
*H02K 7/14* (2006.01)
*H01H 9/06* (2006.01)

(52) U.S. Cl.
CPC .................................. *H01H 9/061* (2013.01)
USPC .............. 318/17; 318/4; 318/5; 318/6; 318/7; 318/8

(58) Field of Classification Search
CPC ........................................................ H01H 9/061
USPC ..................................................... 318/17, 4–9
See application file for complete search history.

(56) References Cited

U.S. PATENT DOCUMENTS

| | | | |
|---|---|---|---|
| 6,019,694 A | 2/2000 | Forrest et al. | |
| 7,707,686 B2 | 5/2010 | Chou | |
| 7,747,349 B2 * | 6/2010 | Yeh et al. | 700/245 |
| 7,823,676 B2 * | 11/2010 | Yamada et al. | 180/218 |
| 8,321,053 B2 * | 11/2012 | Ruan et al. | 700/245 |
| 2006/0277715 A1 | 12/2006 | Lin | |
| 2009/0083938 A1 | 4/2009 | Lin | |
| 2010/0170061 A1 | 7/2010 | Lin | |
| 2011/0067202 A1 | 3/2011 | Chou | |

* cited by examiner

*Primary Examiner* — David Luo
(74) *Attorney, Agent, or Firm* — Armstrong Teasdale LLP

(57) ABSTRACT

A truckle for a mobile medical device is provided. The truckle includes at least one electromagnetism torque balancing motor mounted on the truckle and configured to balance out friction generated by the truckle.

20 Claims, 5 Drawing Sheets

A-phase switch on

B-phase switch on

ELECTROMAGNETISM-TORQUE FRICTION-BALANCING TRUCKLE FOR MOBILE MEDICAL DEVICES

CROSS REFERENCE TO RELATED APPLICATIONS

This application claims the benefit of Chinese Patent Application No. 201010609010.7 filed Dec. 28, 2010, which is hereby incorporated by reference in its entirety.

BACKGROUND OF THE INVENTION

The present invention relates to the mechanical and electrical designs for truckles of medical devices, in particular for truckles of mobile large-scale or heavy medical image diagnostic devices.

When a large-scale or heavy medical image diagnostic device needs to be moved frequently, the operators usually have to push with a lot of strength, so it is very inconvenient. For example, the mobile C-arm X-ray system needs to be moved and positioned frequently during a surgical operation and the device is moved by the handle. Moreover, in some special cases, such as on a soft floor (e.g. a carpet, etc.), since the material of the moving medium has a large friction coefficient, it is harder to move the devices. In addition, such devices are often equipped with more driving motors or include such components as high-energy X-ray generators, flat-panel detectors and cooling systems to meet the demand of the market, increasing the weight and the volume of the whole device. On the other hand, in order to make sure that the users can operate the devices conveniently, design specifications attempt to reduce the operating physical force required as much as possible. For example, one mobile C-arm X-ray system requires that on a tile floor, the starting push force is no more than 12.5 pounds and the rolling push force is no more than 6.0 pounds, and on a nylon carpet floor, the starting push force for a system with a display screen of 9 inches is no more than 45.0 pounds, the starting push force for a system with a display screen of 12 inches is no more than 50.0 pounds, the rolling push force for a system with a display screen of 9 inches is no more than 32.5 pounds, and the rolling push force for a system with a display screen of 12 inches is no more than 35.0 pounds.

SUMMARY OF THE INVENTION

A truckle for mobile medical devices is provided, characterized in that an electromagnetism torque balancing motor is mounted on the truckle to balance out the friction generated by the truckle.

The switch of the electromagnetism torque balancing motor is connected to the handle of the mobile medical device, and the electromagnetism torque balancing motor is powered on by pushing and pulling the handle.

The electromagnetism torque balancing motor is mounted on the bearing of the truckle.

There are two electromagnetism torque balancing motors, which are integrated at the two sides inside the truckle, respectively.

The power of the electromagnetism torque balancing motor on the truckle is selected according to the friction of the floor on which the medical device moves.

If the medical device moves on a soft floor, a high-power electromagnetism torque balancing motor is mounted on the truckle, so that the stall torque of the electromagnetism torque balancing motor is 50-70% of the friction torque.

If the medical device moves on a hard floor, a low-power electromagnetism torque balancing motor is mounted on the truckle, so that the stall torque of the electromagnetism torque balancing motor is 50-70% of the friction torque.

In another aspect, a mobile C-arm X-ray system is provided, including the above described truckle for mobile medical devices, and including a battery connected to the electromagnetism torque balancing motor on the truckle for supplying power thereto.

In yet another aspect, a mobile medical device is provided, including the above described truckle for mobile medical devices, and including a battery connected to the electromagnetism torque balancing motor on the truckle for supplying power thereto.

The embodiments described herein have such advantages as reducing the starting push force and rolling push force during movement of mobile medical devices to realize fast positioning of such kind of devices, and at the same time meeting doctors' requirements on high mobility, maneuverability and flexibility.

DETAILED DESCRIPTION OF THE INVENTION

Exemplary embodiments will be described in detail, but the present invention is not limited thereto.

Exemplary embodiments will be described in detail in conjunction with the drawings, but these embodiments are not intended to limit the present invention. The same components are denoted by the same reference numbers in different drawings.

Figure 1:
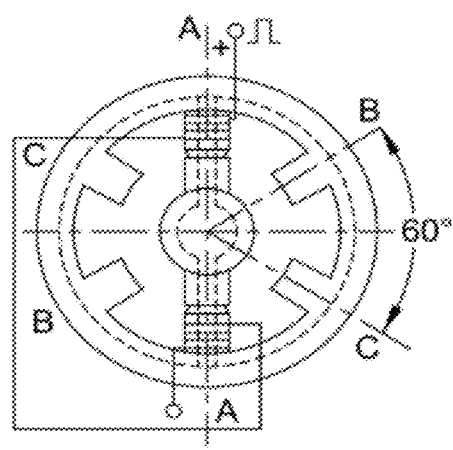
FIG. 1 shows a schematic diagram of an electromagnetism torque balancing motor.
Figure 2A:
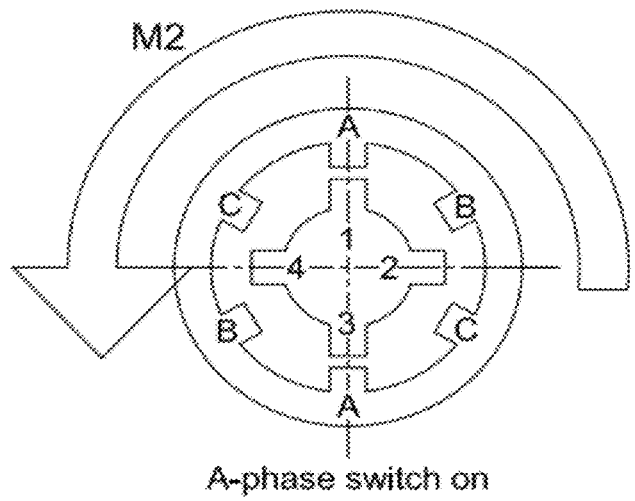
FIGS. 2A and 2B show schematic diagrams of an electromagnetism torque balancing motor.
Figure 2B:
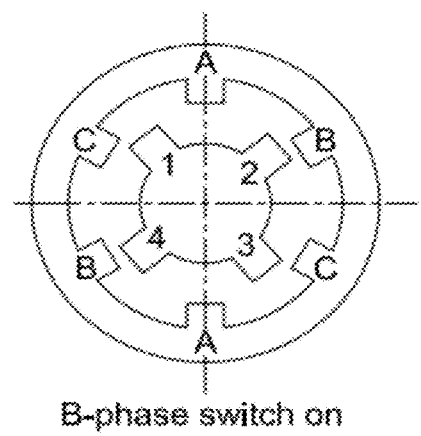

FIG. 1 shows a schematic diagram of an exemplary electromagnetism torque balancing motor. FIG. 2A shows an exemplary torque motor before powering on and FIG. 2B shows that once the electromagnetism torque balancing motor is powered on, it provides a stall torque, i.e. a balance torque M2.

Figure 3:
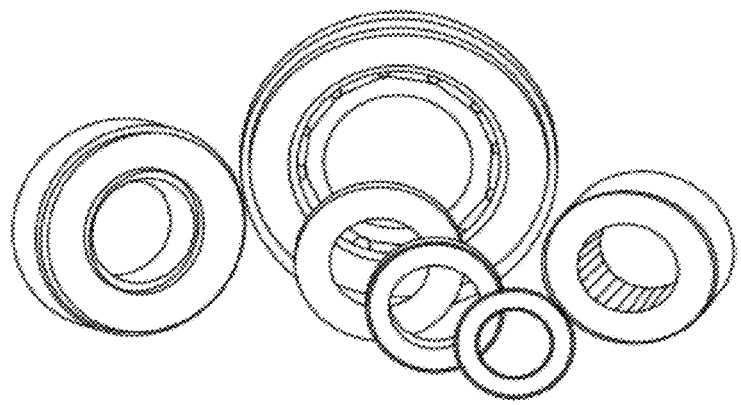
FIG. 3 shows an appearance of a plurality of electromagnetism torque balancing motors.
Figure 4:
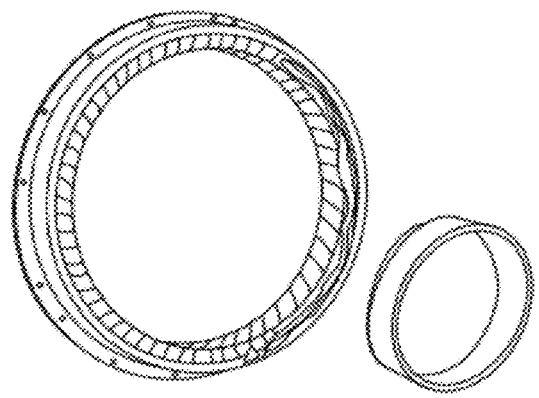
FIG. 4 shows an appearance of a plurality of electromagnetism torque balancing motors.

FIGS. 3 and 4 shows an appearance of a plurality of electromagnetism torque balancing motors. The electromagnetism torque balancing motor can be bought according to the desired parameters.

Figure 5:
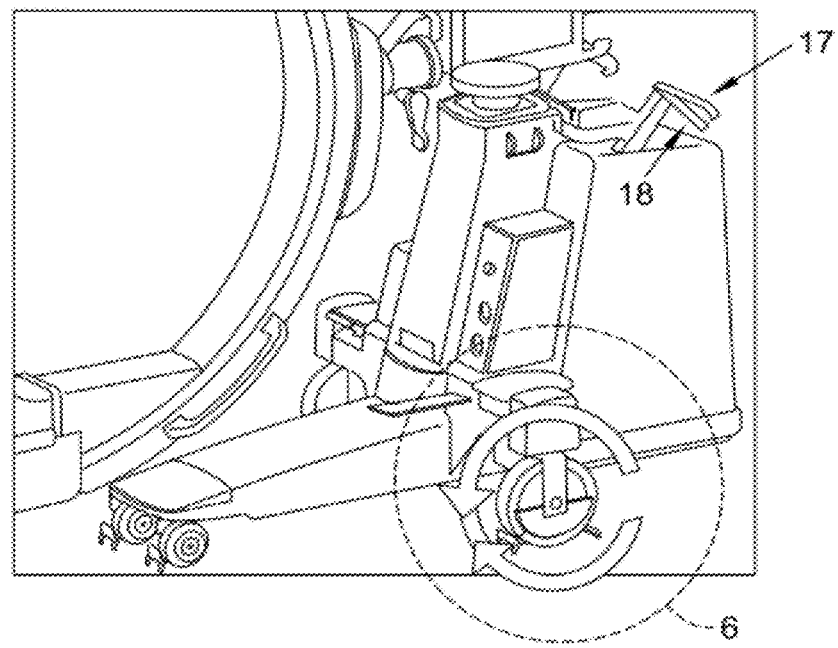
FIG. 5 shows a mechanical structural diagram of an electromagnetism-torque friction-balancing truckle.
Figure 6:
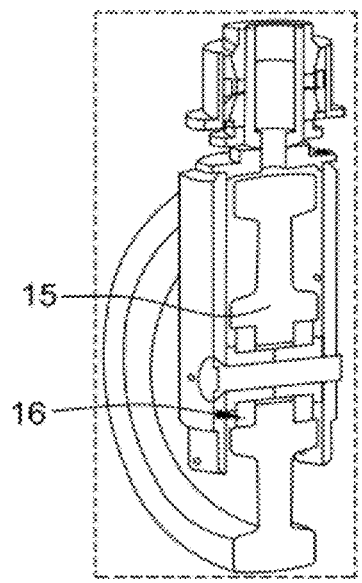
FIG. 6 shows a sectional view of the electromagnetism-torque friction-balancing truckle shown in FIG. 5.

FIG. 5 shows the mechanical structural diagram of an electromagnetism-torque friction-balancing truckle. FIG. 6 shows a sectional view of the electromagnetism-torque friction-balancing truckle shown in FIG. 5. Such a truckle is thinner, and an electromagnetism-torque balancing motor 15 is mounted on the bearing 16 of the truckle, with its switch connected to the handle of the mobile medical device (e.g. mobile C-arm X-ray system). 17 and 18 respectively represent positions where the handle is pulled and pushed. When pushing and pulling the medical device, the electromagnetism-torque balancing motor is powered on to generate a stall torque M2. The needed push force torque before balancing is M1.

$$M1 = F_{starting\ force} = f \times R \times G \times \frac{1}{4},$$

Wherein $F_{starting\ force}$ is the starting push force, f is the conversion factor for unit, R is the radius of the truckle, G is the gravity, which is 9.8 Newtons/meter (N/m), and ¼ represents that the push force is equally distributed on the four truckles.

If, for example, $F_{starting\ force}$=12.5 lbs, f=0.45, R=0.01 m, and G=9.8N/m, then M1=12.5×0.45×0.01×9.8×¼=0.141 N·m.

In the exemplary embodiment, M2 is about 60% of M1, so M2=M1×60%=0.084 N·m.

In some embodiments, a larger stall torque M2 may be desired. For example, some medical devices need to be moved on very soft carpet. For such medical devices, an electromagnetism-torque balancing motor of higher power may be used.

Figure 7:
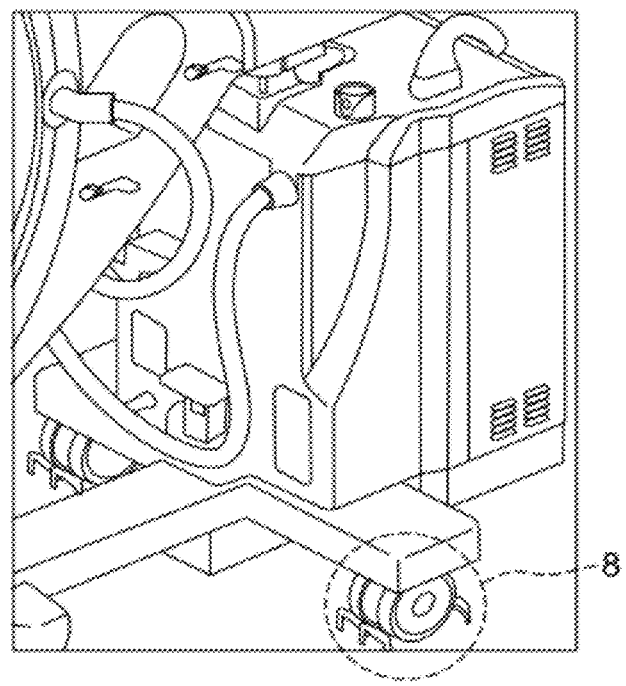
FIG. 7 shows a mechanical structural diagram of an alternative electromagnetism-torque friction-balancing truckle.
Figure 8:
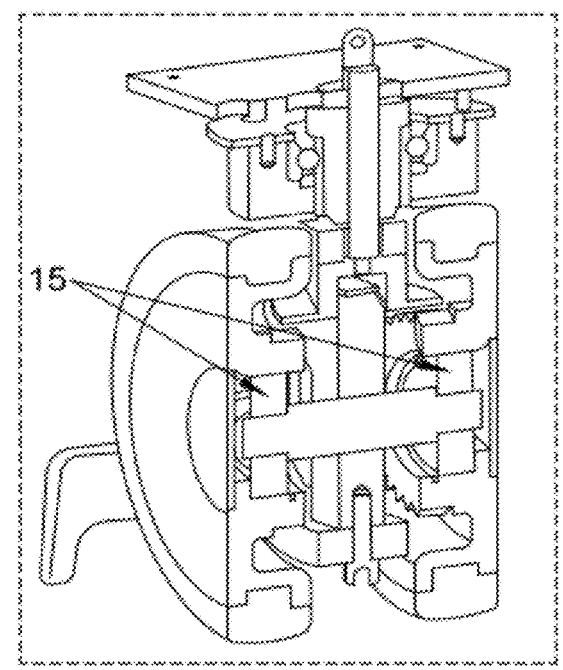
FIG. 8 shows a sectional view of the electromagnetism-torque friction-balancing truckle shown in FIG. 7.

FIG. 7 shows a mechanical structural diagram of an alternative electromagnetism-torque friction-balancing truckle. FIG. 8 shows a sectional view of the electromagnetism-torque friction-balancing truckle shown in FIG. 7. Such truckle is thicker and two electromagnetism-torque motors 15 are respectively integrated at two sides inside the truckle. In addition, a battery may be added on the mobile medical device (e.g. mobile C-arm X-ray system) to supply power to the electromagnetism-torque motors. Once the system is powered down, the system can still be moved substantial distances easily and flexibly using the power generated by the battery.

Figure 9A:
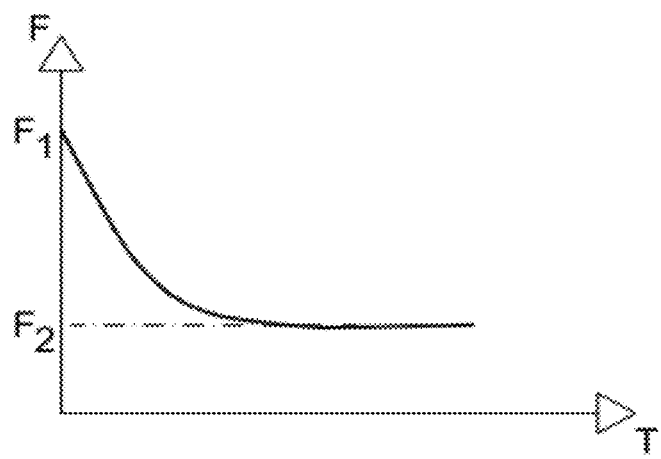
FIGS. 9A and 9B show diagrams of a push force applied to front and back truckles.
Figure 9B:
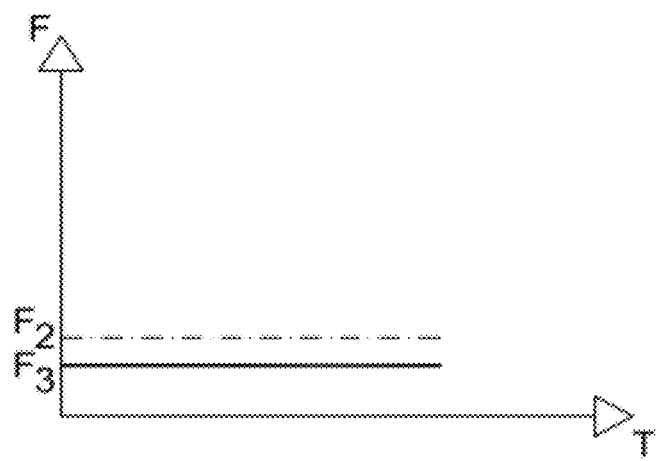

FIGS. 9A and 9B show diagrams of a push force applied to front and back truckles. FIG. 9A shows that the starting push force of the truckle is F1, and the rolling push force is F2. Suppose that the friction torque is M1. When M2 reaches 60% of M1, then FIG. 9B shows that the starting push force and rolling push force needed to move the truckle drops to F3 when utilizing the electromagnetism-torque balancing motor. In the exemplary embodiment, F3 is about 50-70% of F2, for example 60%.

The method of reducing friction resistance described herein can also be applied to other mobile medical image diagnostic devices and other mobile medical devices in addition to the mobile C-arm X-ray system.

The exemplary embodiments are only illustration. It shall be noted that those of ordinary skill in the art will be able to make many improvements, modifications and variations without departing from the spirit of the present invention. Such improvements, modifications, and variations shall be considered as falling within the scope of the present application.

The invention claimed is:

1. A truckle for a mobile medical device comprising at least one electromagnetism torque balancing motor mounted on the truckle and configured to balance out friction between the truckle and a floor on which the mobile medical device moves.

2. The truckle for a mobile medical device according to claim 1, wherein a switch of the at least one electromagnetism torque balancing motor is connected to a handle of the mobile medical device, and wherein the electromagnetism torque balancing motor is configured to be powered on by pushing the handle.

3. The truckle for a mobile medical device according to claim 1, wherein the at least one electromagnetism torque balancing motor is mounted on a bearing of the truckle.

4. The truckle for a mobile medical device according to claim 1, wherein the at least one electromagnetism torque motor comprises two electromagnetism torque balancing motors integrated at two respective sides inside the truckle.

5. The truckle for a mobile medical device according to claim 1, wherein a power of the at least one electromagnetism torque balancing motor is selected based on a friction of the floor on which the mobile medical device moves.

6. The truckle for a mobile medical device according to claim 5, wherein the at least one electromagnetism torque motor comprises a high-power electromagnetism torque balancing motor mounted on the truckle, such that a stall torque of the electromagnetism torque balancing motor is 50-70% of a friction torque when the mobile medical device is moved on a soft floor.

7. The truckle for a mobile medical device according to claim 5, wherein the at least one electromagnetism torque motor comprises a low-power electromagnetism torque balancing motor mounted on the truckle, such that a stall torque of the electromagnetism torque balancing motor is 50-70% of a friction torque when the mobile medical device is moved on a hard floor.

8. A mobile medical device comprising the truckle according to claim 1.

9. The mobile medical device according to claim 8, further comprising a battery connected to the electromagnetism torque balancing motor and configured to supply power thereto.

10. The truckle for a mobile medical device according to claim 1, wherein a switch of the at least one electromagnetism torque balancing motor is connected to a handle of the mobile medical device, and wherein the electromagnetism torque balancing motor is configured to be powered on by pulling the handle.

11. A mobile C-arm X-ray system comprising:
a truckle; and
at least one electromagnetism torque balancing motor mounted on the truckle and configured to balance out friction between the truckle and a floor on which the mobile C-arm X-ray system moves.

12. The mobile C-arm X-ray system according to claim 11, further comprising a battery connected to the at least one electromagnetism torque balancing motor and configured to supply power thereto.

13. The mobile C-arm X-ray system according to claim 11, wherein a power of the at least one electromagnetism torque balancing motor is selected based on a friction of the floor on which the mobile C-arm X-ray system moves.

14. The mobile C-arm X-ray system according to claim 13, wherein the at least one electromagnetism torque motor comprises a high-power electromagnetism torque balancing motor mounted on the truckle, such that a stall torque of the electromagnetism torque balancing motor is 50-70% of a friction torque when the mobile C-arm X-ray system is moved on a soft floor.

15. The mobile C-arm X-ray system according to claim 13, wherein the at least one electromagnetism torque motor comprises a low-power electromagnetism torque balancing motor mounted on the truckle, such that a stall torque of the electromagnetism torque balancing motor is 50-70% of a friction torque when the mobile C-arm X-ray system is moved on a hard floor.

16. A method for assembling a mobile medical device that includes at least one truckle, the method comprising coupling at least one electromagnetism torque balancing motor to the truckle, the at least one electromagnetism torque balancing motor configured to balance out friction between the truckle and a floor during movement of the mobile medical device across the floor.

17. The method according to claim 16, further comprising coupling a switch of the at least one electromagnetism torque balancing motor to a handle of the mobile medical device such that the electromagnetism torque balancing motor is powered on when the handle is pushed.

18. The method according to claim 16, further comprising coupling a switch of the at least one electromagnetism torque balancing motor to a handle of the mobile medical device such that the electromagnetism torque balancing motor is powered on when the handle is pulled.

19. The method according to claim 16, further comprising coupling a battery to the at least one electromagnetism torque balancing motor, wherein the battery is configured to supply power to the at least one electromagnetism torque balancing motor.

20. The method according to claim 16, wherein coupling at least one electromagnetism torque balancing motor to the truckle comprises coupling an electromagnetism torque balancing motor on each side of the truckle.

* * * * *